(12) United States Patent
May et al.

(10) Patent No.: US 7,005,851 B2
(45) Date of Patent: Feb. 28, 2006

(54) METHODS AND APPARATUS FOR INSPECTION UTILIZING PULSED EDDY CURRENT

(75) Inventors: Andrew May, Schenectady, NY (US); Changting Wang, Schenectady, NY (US); Yuri Alexeyevich Plotnikov, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 175 days.

(21) Appl. No.: 10/675,822

(22) Filed: Sep. 30, 2003

(65) Prior Publication Data

US 2005/0068026 A1  Mar. 31, 2005

(51) Int. Cl.
*G01N 27/72* (2006.01)
(52) U.S. Cl. ............... 324/228; 324/716; 324/242; 324/207.12; 73/38; 345/174
(58) Field of Classification Search ........... 324/228, 324/716, 242, 207.12; 73/38; 345/174
See application file for complete search history.

(56) References Cited

U.S. PATENT DOCUMENTS

| | | | |
|---|---|---|---|
| 4,000,458 A | * | 12/1976 | Miller et al. ............ 324/236 |
| 4,843,320 A | | 6/1989 | Spies |
| 4,990,851 A | | 2/1991 | Spies |
| 5,028,100 A | | 7/1991 | Valleau et al. |
| 5,034,689 A | * | 7/1991 | Inoue et al. ............ 324/225 |
| 5,623,427 A | | 4/1997 | Vandervalk et al. |
| 5,847,562 A | * | 12/1998 | Fulton et al. ............ 324/229 |
| 6,037,768 A | | 3/2000 | Moulder et al. |
| 6,188,969 B1 | * | 2/2001 | Minor ............ 702/86 |
| 6,291,992 B1 | | 9/2001 | Van Andel et al. |
| 6,344,741 B1 | | 2/2002 | Giguere et al. |
| 6,876,949 B1 | * | 4/2005 | Hilliard et al. ............ 702/182 |
| 2002/0190724 A1 | | 12/2002 | Plotnikov et al. |

FOREIGN PATENT DOCUMENTS

EP     0631147 A1 *  6/1994

* cited by examiner

*Primary Examiner*—Michael Tokar
*Assistant Examiner*—Diane E. Jones
(74) *Attorney, Agent, or Firm*—Penny A. Clarke; Patrick K. Patnode

(57) ABSTRACT

In some aspects, the present invention provides a method for estimating at least one measurement/object property of a metal object. The method includes generating a time-varying eddy current in a wall of the metal object utilizing a pulsed-signal transmitter. The method further includes measuring the time-varying eddy current, fitting the time-varying measured eddy current to a parameterized polynomial, and interpreting the parameterized polynomial to determine one or more measurement/object properties of the metal object.

31 Claims, 3 Drawing Sheets

METHODS AND APPARATUS FOR INSPECTION UTILIZING PULSED EDDY CURRENT

BACKGROUND OF THE INVENTION

This invention relates generally to nondestructive evaluation of metallic structures and more particularly to methods and apparatus for inspecting electrically conductive material.

Surface cracks and subsurface flaws in metallic structures can produce catastrophic failures in critical components or structural elements. Eddy current probes can be used to determine the severity of such cracks and flaws in the case of metallic components and structural elements. Configurations of pulsed eddy current two-dimensional array probes are known that utilize a two-dimensional sensor array probe system with a data visualization component for electrically conducting component inspection. The probe uses a two-dimensional array of magnetic field sensors for inspection of electrically conducting components without requiring mechanical scanning.

Metallic objects can also suffer corrosion loss. For example, a wall of a steel container, a pipe, or a plate may be locally affected by corrosion. In some cases, visual inspection of the corroded region may be impractical because of lack of access to the corroded region. Inspection of such objects may require a through-transmission technique that can detect corrosion on one side of the object with a sensor located on the opposite side. Pulsed eddy current is known to be capable of this type of measurement in conducting materials. However, the pulsed eddy current can be difficult to interpret quantitatively because the relationship between the response and the material properties of some objects is complex. For example, a pipeline or vessel wall may be so dirty as to preclude a visual inspection of the object. Moreover, a significant and spatially varying stand-off may be presented between the pulsed eddy current sensor and the actual surface of the object. This stand-off further complicates interpretation of eddy current responses.

BRIEF DESCRIPTION OF THE INVENTION

Some configurations of the invention therefore provide a method for estimating at least one measurement/object property of a metal object. The method includes generating a time-varying eddy current in a wall of the metal object utilizing a pulsed-signal transmitter. The method further includes measuring the time-varying eddy current, fitting the time-varying measured eddy current to a parameterized polynomial, and interpreting the parameterized polynomial to determine one or more measurement/object properties of the metal object.

Various configurations of the present invention provide an apparatus for estimating at least one measurement/object property of a metal object. The apparatus includes a drive coil and a pulse generator operable to energize the drive coil in a pulsed manner to transmit a transient electromagnetic flux to into a metal object under inspection. The apparatus also includes at least one sensor operable to sense and generate output signals representative of time varying eddy currents produced in the metal object under inspection form the transient electromagnetic flux. A processor operatively coupled to the sensor or sensors is also provided. The processor is configured to measure the output signals representative of the time-varying eddy currents resulting from the transient electromagnetic flux, fit the measured output signal to a parameterized polynomial, and interpret the parameterized polynomial to determine one or more measurement/object property of the metal object.

It will be appreciated that various configurations of the present invention provide accurate estimates of sensor lift-off, sample permeability, conductivity, and thickness conditions even under adverse and/or indeterminate measurement conditions. Furthermore, parameterizations used in some configurations do not require computation of logarithms and thus avoid computational instabilities in the presence of noise. In many configurations, thermal drift effects of amplifier gain and power supply variation are also minimized.

DETAILED DESCRIPTION OF THE INVENTION

Fitting a polynomial curve to pulsed eddy current response data has been empirically found to provide a good fit to data over a typical range of conditions expected during normal operation of a pulsed eddy current sensor in various applications. More particularly, a good fit has been found under a typical expected range of sensor lift-off, sample permeability, conductivity, and thickness conditions. Thus, a technical effect of the methods described herein is the indirect measurement of one or more measurement/object parameters of a metallic object utilizing a physical test.

Coefficients of the curve are therefore utilized in some configurations of the present invention to fit a non-linear transfer function relating the fit coefficients to the thickness, permeability, conductivity, and lift-off of samples from which the responses were measured. On subsequent measurements of samples with unknown physical parameters, a pulsed eddy current response is measured and parameterized. The previously computed transfer function is used to interpret the fit coefficients and estimate the physical parameters and sensor liftoff. The magnitude of the pulsed eddy current measurement will reach zero over time, so it is advantageous that parameterization by polynomial fitting does not require that the logarithm of the dependent variable be computed. As a result, computational instabilities in the presence of noise are avoided.

Parameterization produces a constant term, $a_0$, which represent a DC offset of the measurement system. This term has no relation to the material properties of interest and is discarded in some configurations of the present invention.

Some configurations then divide the remaining coefficients of the curve by an $a_1$ (linear) coefficient. This division advantageously removes thermal drift effects of amplifier gain and power supply variation. In addition, effects of batch-to-batch variation between manufacturing runs of the pulsed eddy current sensor itself are reduced. Some configurations of the present invention then use the remaining normalized coefficients $a_2$ to $a_n$ to fit a non-linear transfer function relating the fit coefficients to the thickness, permeability and liftoff of the samples from which the responses were measured. On subsequent measurements on samples with unknown physical parameters, the measured pulsed eddy current is parameterized and the previously computed transfer function is used to interpret the fit coefficients and estimate the physical parameters and sensor liftoff.

Figure 1:
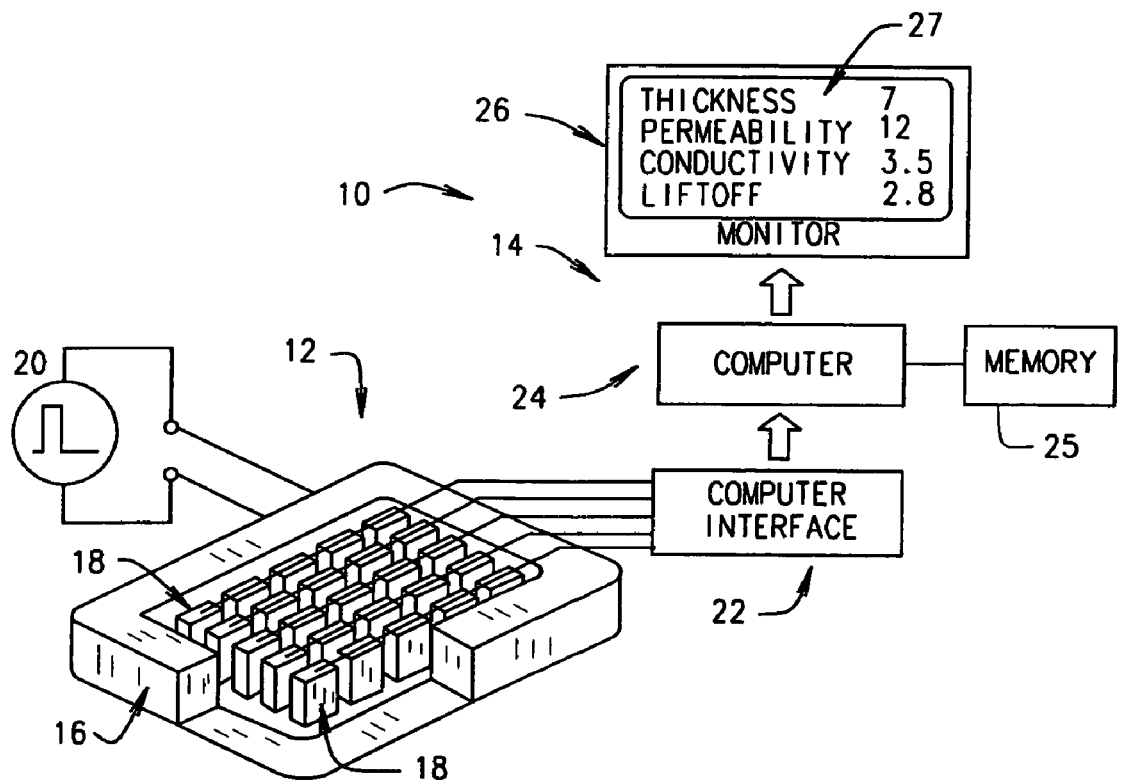
FIG. 1 is a diagrammatic representation of various configurations of an eddy current inspection apparatus of the present invention.

Thus, in some configurations and referring to FIG. 1, a non-destructive eddy current-based measurement system 10 comprises an eddy current sensor array probe 12 and a data acquisition apparatus 14. Although sensor array probe 12 is shown here as a two-dimensional sensor array similar to that disclosed in U.S. patent Publication No. US 2002/0190724 A1 of Ser. No. 09/681,824, filed Jun. 12, 2001 and assigned to General Electric Company, configurations of the present invention do not necessarily require either a two-dimensional sensor array or the two-capabilities disclosed in that Patent Publication.

Array probe 12 includes a drive coil 16, which is shown partially cut away in FIG. 1 to reveal more details of an included sensor or sensors 18, and a square pulse generator 20. Data acquisition apparatus 14 includes a computer interface 22, a computer 24, such as a personal computer with memory 25, and a monitor 26. Drive coil 16 is a multiple turn solenoid that can be of generally rectangular configuration surrounding sensor or sensors 18. Sensors 18 can be located inside or outside as well as above or below drive coil 16. Rectangular drive coil 16 is used to transmit a transient electromagnetic flux into a metallic object under test. Memory 25 in FIG. 1 is intended to represent one or more volatile and/or nonvolatile storage facilities not shown separately that are familiar to those skilled in the art. Examples of such storage facilities often used with computers 24 include solid state memory (e.g., random access memory (RAM), read-only memory (ROM), and flash memory), magnetic storage devices (e.g., floppy disks and hard disks), optical storage devices (e.g., CD-ROM, CD-RW, and DVD), and so forth. This memory may be internal to or external to computer 24.

Figure 2:
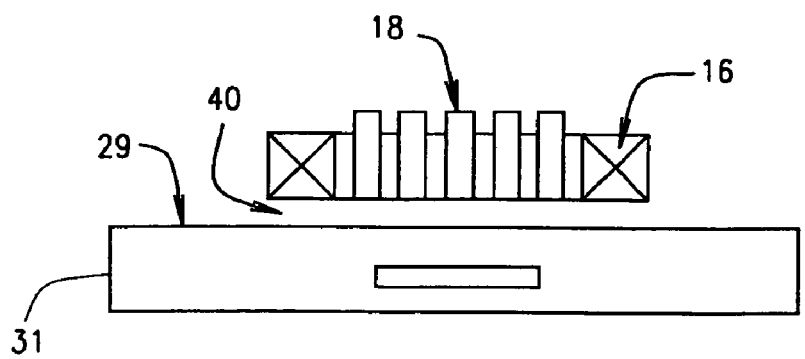
FIG. 2 is a diagrammatic representation of a configuration of an eddy current inspection apparatus represented in FIG. 1 as used to inspect a metal object.
Figure 3:
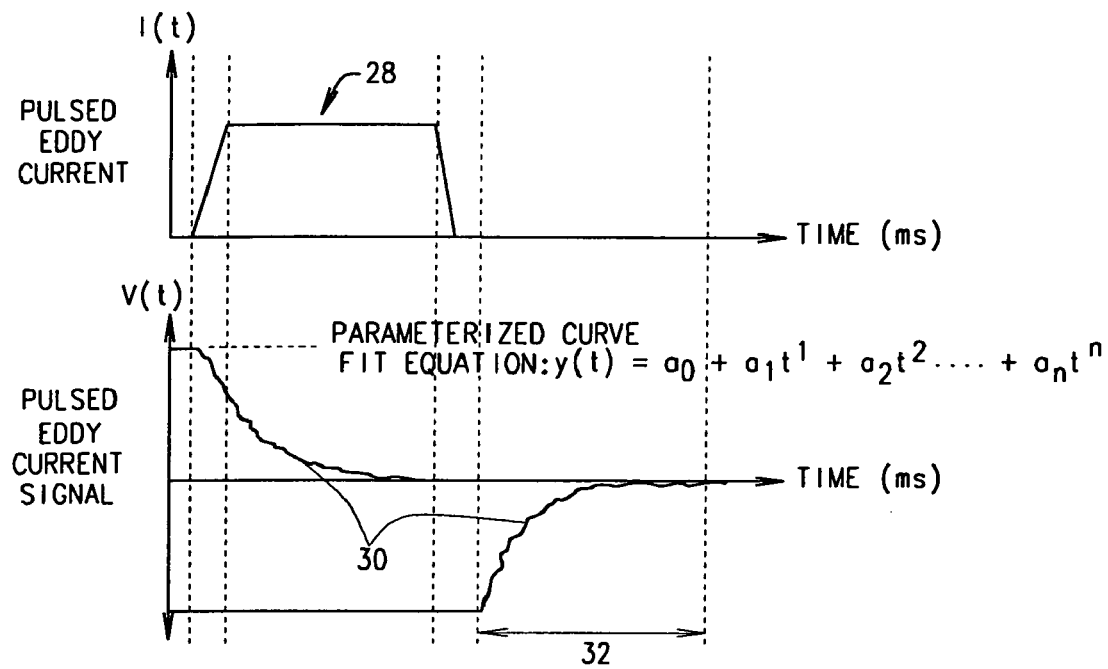
FIG. 3 is a representation of pulsed eddy current waveforms and a parameterized curve used to fit a pulsed eddy current signal.

Referring to FIGS. 1, 2, and 3, pulse generator 20 is used to excite drive coil 16 with an essentially rectangular-shaped short duration pulse 28 of electrical current while sensors 18 and coil 16 are on or proximate a surface 29 of a metal object 31. As a result, a pulsed eddy current 30 is generated in a metal object under test (not shown). In some configurations in which the metal object is thin (5 mm thick) steel, the duration of the pulse is 10 ms to provide rapid measurements and/or significant signal averaging to improve the signal to noise ratio. In some configurations in which the metal object is a thicker sample (e.g., 12 mm or more), the duration of the pulse is up to 200 ms. Still other configurations utilize 300 ms pulses. In each of these configurations, sensor or sensors 18 sense the pulsed eddy current 30 as a voltage. For example, pulsed eddy current 30 might produce a signal ranging from +500 mV to −500 mV in sensor or sensors 18 for a particular test sample. For the sake of simplicity, only a signal generated by one sensor 18 is considered for the remainder of this discussion, as a plurality of sensors is not required to practice many configurations of the present invention. Also, a sensor that measures pulsed eddy current may produce either a voltage or a current indicative of the pulsed eddy current. Therefore, "a measured eddy current," as used herein, includes any measured representation of the eddy current, whether the representation is in the form of a voltage, a current, or a digitized value.

Computer interface 22 receives response signal 30 from sensor 18 and communicates a digitized signal representative of pulsed eddy current 30 during a measurement window 32 into computer 24. Measurement window 32 commences very shortly after pulse 28 ends. For example, in some configurations, measurement window 32 begins 10 ms afterwards in some configurations. In other configurations, measurement window 32 begins 0.5 ms afterwards to provide improved measurement of sensor liftoff. Utilizing a stored program in memory 25, computer 24 parameterizes this digitized signal and applies a transfer function to the parameters to determine at least one measurement/object property. As used herein, a "measurement/object property" is a physical property of the metallic object itself, such as wall thickness, permeability, or conductivity, and/or a property of the measurement, i.e., a physical relationship between the metallic object and the sensor, such as sensor liftoff. Result 27 can be displayed on display 26 and/or saved in memory 25 and/or printed on a printer (not shown in the figures) for later use.

Figure 4:
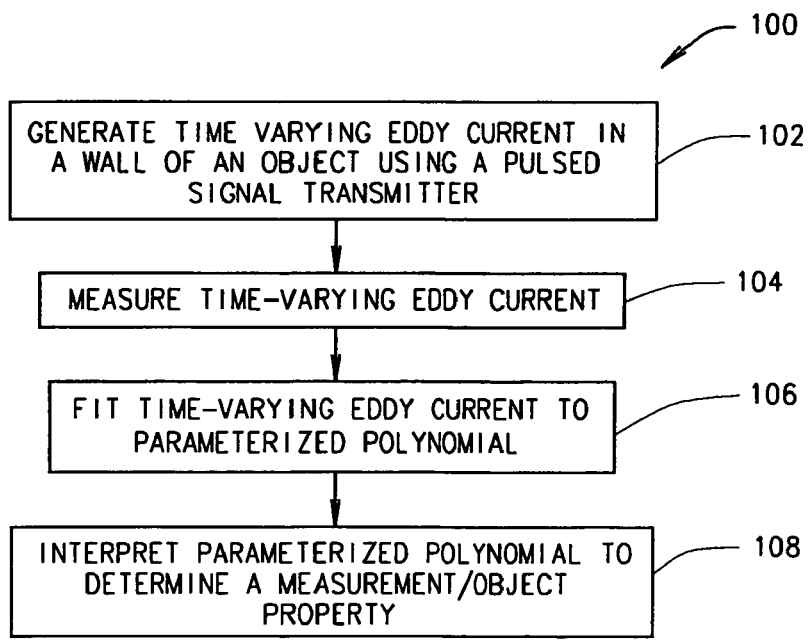
FIG. 4 is a flow chart representative of various methods for determining measurement/object properties of a metallic object.
Figure 5:
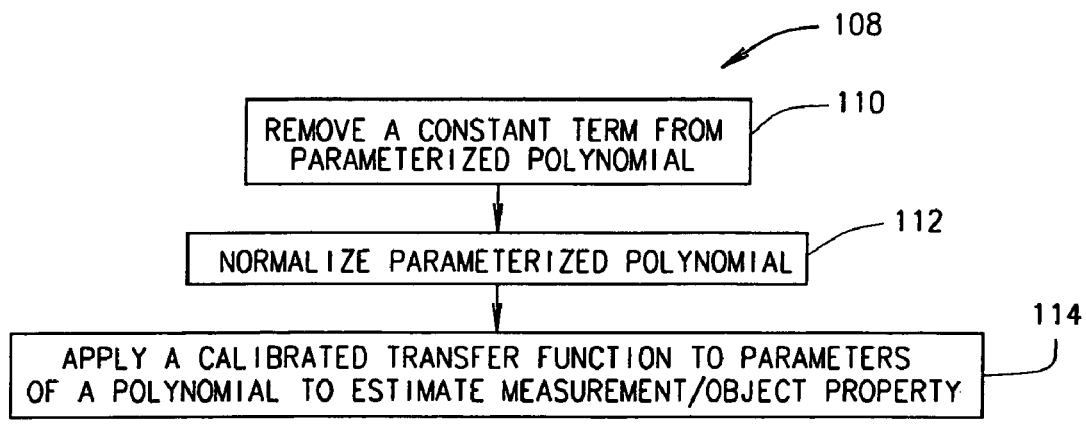
FIG. 5 is a flow chart representative of various methods for interpreting a measurement polynomial to determine measurement/object properties of a metallic object.

Referring to FIGS. 4 and 5, a flow chart 100 is shown that is representative of various configurations of the present invention. A technical effect of processes represented by flow chart 100 is the physical measurement of at least one measurement/object property of a metal object. These processes include generating, at 102, a time-varying eddy current 30 in a wall of the metal object using a pulsed signal transmitter. A pulse generator may, for example, comprise the combination of drive coil 16 and pulse generator 20. The resulting time-varying eddy current 30 is measured at 104, for example, during a measurement window 32 shortly following the termination of excitation pulse 28. In many configurations, this measurement is digitized by computer interface 22.

The measurements from 104 are then fitted at 106 by computer 24 to a parameterized curve using a stored program in memory 25. For example, the measurements are fitted to an equation $v(t)=a_0+a_1t^{-1}+a_2t^{-2}+ \ldots +a_nt^{-n}$, where $a_0$ is an offset parameter and $a_1$ is a normalization parameter. The number of terms n is a parameter that is derived from experimental results, as explained below. Some configurations select an origin for time t different from that of the beginning or end of excitation pulse 28. For example, either the time at the beginning of measurement window 32 or the time at which a peak magnitude of the measured eddy current occurs within measurement window 32 can be defined as t=0 in various configurations.

Next, at 108, the parameterized polynomial is interpreted to determine at least one measurement/object property of the metal object. The measurements/object property or properties may include one of more of wall thickness, permeability, conductivity, and/or sensor liftoff.

Referring to FIG. 5, more details of the interpretation of the parameterized polynomial at 108 are shown. This interpretation comprises, in various configurations, removing a constant term from the parameterization at 110. Thus, in the polynomial $a_0+a_1t^{-1}+a_2t^{-2}+ \ldots +a_nt^{-n}$, the term $a_0$ is removed. In some configurations, "removal" is accomplished by simply ignoring this term in interpreting the polynomial. At 112, some configurations also normalize the polynomial. This normalization can be accomplished by dividing the entire polynomial by the coefficient of the $t^{-1}$ term, $a_1$, except that the $a_0$ term need not be included in the division in configurations in which it is ignored or removed. A calibrated transfer function is applied to the remaining parameters of the polynomial $a_2/a_1, a_3/a_1, \ldots, a_n/a_1$ at 114 to estimate a measurement/object property. In particular, one or more measurement/object properties $Y_i$ is estimated by determining a value of $Y_i = f_i(a_2/a_1, \ldots, a_n/a_1)$, where i in this expression is simply an arbitrary index indicating that each measurement/object property is determined by a different function $f_i(\ )$. (The use of a matrix-valued function to determine more than one measurement/object property is considered to be no different from, or at least equivalent to applying different functions for each measurement/object property.) The measurement/object property or property may include wall thickness, i.e., thickness of the metal object beneath the eddy current sensor, permeability, conductivity, and sensor liftoff, or any combination of these.

Figure 6:
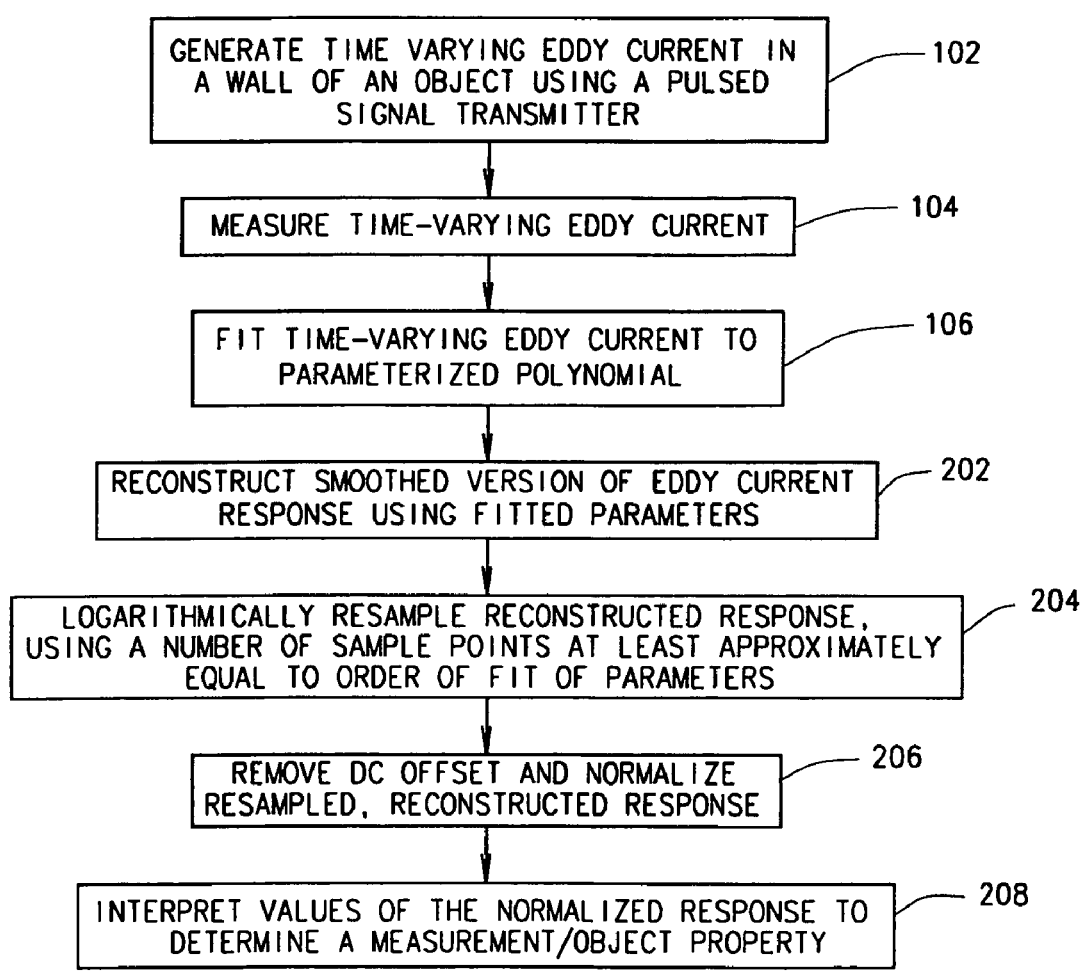
FIG. 6 is a flow chart representative of other various methods for processing and interpreting a time-varying eddy current to detect measurement/object properties of a metallic object.

Referring now to FIG. 6, a flow chart 200 is shown that is representative of some configurations of the present invention that do not directly use fitted parameters to measure at least one measurement/object property of a metal object. A technical effect of processes represented by flow chart 200 is the physical measurement of at least one measurement/object property of a metal object. Configurations using these processes differ in what is done after generation of the eddy current at 102, its measurement at 104, and its fitting to a parmeterized polynomial at 106 are performed. More specifically, a smoothed version of the time varying eddy current is reconstructed at 202 from the fitted parameters. The reconstructed response curve is then resampled, using a number of sample points at least approximately equal to the order of fit of the parameters at 204. In some configurations, the resampling is logarithmic, i.e., more data points are taken from the beginning part of the fitted reconstructed response than from the end. Logarithmic resampling advantageously gives greater emphasis to the initial portion of the response, which contains more information about the measurement/object properties than does the remainder of the response. Using a number of sampling points at least approximately equal to the order of fit of the parameters provides a reasonably good match with the number of degrees of freedom remaining in the reconstructed response. Thus, the sample points contain all or most of the information in the reconstructed response without much redundancy. At 206, the DC offset of the resampled, reconstructed response is removed. In some configurations, the DC office is removed by subtracting the value of the last point in the reconstructed curve from the value at all other points of the curve. Also at 206, the curve is normalized. In some configurations, this normalization is performed after the DC office is removed by dividing all values of the curve by the value of the reconstructed curve at t=1 ms. Next, values of the normalized response are interpreted at 208 to determine a measurement/object property. For example, in some configurations, the values of the normalized response at predetermined number of predetermined times (such as some or all of the logarithmic sample points described above) are used as parameters to which a calibrated transfer function is applied. This transfer function is analogous to the transfer function used at 114 in FIG. 5, but in general will be different from the transfer function at 114 because the parameters are not coefficients of a polynomial, but rather values of a (normalized) reconstructed response at certain specified times. The procedures for determining the transfer function to be used at 208 are correspondingly different, but in some configurations also involve a statistical fit.

The various configurations represented by FIG. 6 are described herein as alternatives to the various configurations represented by FIG. 4 and FIG. 5. However, nothing about the present invention prevents or prohibits utilizing both alternatives in one configuration, providing a selection of both alternatives in one configuration, or further processing or averaging results for the same parameter obtained from both alternatives to derive a possibly improved estimate of the parameter.

Methods such as those described above are particularly useful for measuring properties of metallic objects that are inaccessible for visual inspection and/or are rusted, corroded, dirty, or partially buried. In such cases, and referring to FIG. 6, it may be difficult to determine from visual inspection whether a standoff (i.e., liftoff 40) exists between eddy current sensor 18 and surface 29 of metallic object 31. However, an empirical correction for liftoff is incorporated in the transfer function or functions used to estimate the measurement/object properties, and/or a function is provided to estimate the liftoff distance, itself. The calibrated transfer functions in various configurations of the present invention can include non-linear functions of the fitted parameters.

Calibrated transfer functions in some configurations of the present invention are determined in advance and stored in memory 25 of computer 24. More particularly, independent measurements are made on calibration samples of metallic objects. In some configurations, some or all of the independent measurements may be replaced with results from parameters used in finite element computational simulations of sensor lift-off, permeability, conductivity, and/or thickness. Pulsed eddy current responses are measured from the calibration samples (or are produced from finite element computational models) and these responses are fitted to a polynomial curve using a method such as that described in conjunction with FIGS. 3 and 4. However, rather than analyzing the parameterized curve using a transfer function to determine the measurement/object properties of a metallic object, parameters of the parameterized curve and the measured (or computationally simulated) measurement/object properties are used to derive the transfer function or functions $Y_i = f_i(a_2/a_1, a_3/a_1, \ldots, a_n/a_1)$. The nature of each transfer function is determined empirically, in some configurations, by the shape of a curve that approximates the available data. Because the fit is empirical, a non-linear transfer function may be approximated as a sufficiently close-fitting multivariate polynomial or other function suggested by the data, at least within the range of experimental or simulated observation.

Because the determination of the transfer function or functions $f_i$ proceeds empirically, the number of terms n in the parameterization of an eddy current response is also determined empirically, as are suitable transfer functions $f_i$. However, to provide for a degree of independence between estimated parameters, some configurations use a polynomial having at least one parameter for each measurement/object property to be estimated, after taking into account removed parameters and parameters used only for normalization. Thus, if the four measurement/object properties sensor liftoff, permeability, conductivity, and thickness are all to be estimated, at least a fifth degree polynomial is fitted to the eddy current response (because the $a_0$ term is ignored and the $a_1$ term is used for normalization) in some configurations. Higher degree polynomials can also be used.

While the invention has been described in terms of various specific embodiments, those skilled in the art will recognize that the invention can be practiced with modification within the spirit and scope of the claims.

What is claimed is:

1. A method for estimating at least one measurement/object property of a metal object, said method comprising:
generating a time-varying eddy current in a wall of the metal object utilizing a pulsed-signal transmitter;
measuring the time-varying eddy current;
fitting said time-varying measured eddy current to a parameterized polynomial; and
interpreting the parameterized polynomial to determine the at least one measurement/object property of the metal object, wherein said interpreting the parameterized polynomial further comprises removing a constant term from the polynomial.

2. A method for estimating at least one measurement/object property of a metal object, said method comprising:
generating a time-varying eddy current in a wall of the metal object utilizing a pulsed-signal transmitter;
measuring the time-varying eddy current;
fitting said time-varying measured eddy current to a parameterized polynomial; and
interpreting the parameterized polynomial to determine the at least one measurement/object property of the metal object,
wherein said interpreting the parameterized polynomial further comprises normalizing the polynomial to a unit first power term.

3. A method in accordance with claim 2 wherein said interpreting the parameterized polynomial comprises applying a calibrated transfer function to parameters of the normalized parameterized polynomial to estimate a measurement/object property.

4. A method in accordance with claim 3 wherein said measurement/object property is wall thickness.

5. A method in accordance with claim 3 wherein said measurement/object property is permeability.

6. A method in accordance with claim 3 wherein said measurement/object property is conductivity.

7. A method in accordance with claim 3 wherein said measurement/object property is sensor liftoff.

8. A method in accordance with claim 3 wherein said measurement/object property is selected from the group consisting of wall thickness, permeability, conductivity, and sensor liftoff, and further wherein said metallic object is inaccessible to visual inspection and said measuring a time-varying eddy current resulting from said generated magnetic field comprises measuring said eddy current utilizing a sensor having an indeterminate standoff from a surface of the metallic object.

9. A method in accordance with claim 3 wherein said transfer function is a non-linear transfer function.

10. A method in accordance with claim 3 further comprising deriving said transfer function utilizing independent measurements on calibration samples.

11. A method in accordance with claim 3 further comprising deriving said transfer function utilizing finite element computational simulations.

12. An apparatus for estimating at least one measurement/object property of a metal object, said apparatus comprising:
a drive coil;
a pulse generator operable to energize said drive coil in a pulsed manner to transmit a transient electromagnetic flux to into a metal object under inspection;
at least one sensor operable to sense and generate output signals representative of time varying eddy currents produced in the metal object under inspection from said transient electromagnetic flux;
a processor operatively coupled to said at least one sensor and configured to:
measure the output signals representative of the time-varying eddy currents resulting from said transient electromagnetic flux;
fit the measured output signal to a parameterized polynomial; and
interpret the parameterized polynomial to determine the at least one measurement/object property of the metal object, wherein to interpret the parameterized polynomial, said apparatus is configured to remove a constant term from the polynomial.

13. An apparatus for estimating at least one measurement/object property of a metal object, said apparatus comprising:
a drive coil;
a pulse generator operable to energize said drive coil in a pulsed manner to transmit a transient electromagnetic flux to into a metal object under inspection;
at least one sensor operable to sense and generate output signals representative of time varying eddy currents produced in the metal object under inspection from said transient electromagnetic flux;
a processor operatively coupled to said at least one sensor and configured to:
measure the output signals representative of the time-varying eddy currents resulting from said transient electromagnetic flux;
fit the measured output signal to a parameterized polynomial; and
interpret the parameterized polynomial to determine the at least one measurement/object property of the metal object,
wherein to interpret the parameterized polynomial said apparatus is configured to normalize the polynomial.

14. An apparatus in accordance with claim 13 wherein to interpret the parameterized polynomial, said apparatus is configured to apply a calibrated transfer function to parameters of the normalized parameterized polynomial to estimate a measurement/object property.

15. An apparatus in accordance with claim 14 wherein said measurement/object property is wall thickness.

16. An apparatus in accordance with claim 14 wherein said measurement/object property is permeability.

17. An apparatus in accordance with claim 14 wherein said measurement/object property is conductivity.

18. An apparatus in accordance with claim 14 wherein said measurement/object property is sensor liftoff.

19. An apparatus in accordance with claim 14 wherein said measurement/object property one or more measurement/object property selected from the group consisting of wall thickness, permeability, conductivity, and sensor liftoff.

20. An apparatus in accordance with claim 14 wherein said transfer function is a non-linear transfer function.

21. An apparatus in accordance with claim 14 wherein said processor further comprises a memory, and said transfer function is stored in said memory.

22. An apparatus for estimating at least one measurement/object property of a metal object, said apparatus comprising:
a drive coil;
a pulse generator operable to energize said drive coil in a pulsed manner to transmit a transient electromagnetic flux to into a metal object under inspection;

at least one sensor operable to sense and generate output signals representative of time varying eddy currents produced in the metal object under inspection from said transient electromagnetic flux;

a processor operatively coupled to said at least one sensor and configured to:

measure the output signals representative of the time-varying eddy currents resulting from said transient electromagnetic flux;

fit said output signals to a parameterized polynomial;

reconstruct a smoothed version of the measured eddy current using fitted parameters of the parameterized polynomial;

resample the reconstructed eddy current using a number of sample points; and interpret the reconstructed eddy current to determine a measurement/object property of the metal object.

23. An apparatus in accordance with claim 22 wherein to resample the reconstructed eddy current, said apparatus is configured to logarithmically resample the reconstructed eddy current.

24. An apparatus in accordance with claim 22 configured to resample the reconstructed eddy current using a number of sample points approximately equal to an order of fit of the fitted parameters.

25. An apparatus in accordance with claim 24 wherein said resampling comprises logarithmic resampling.

26. An apparatus in accordance with claim 22 further configured to remove a DC offset from and normalize the resampled, reconstructed eddy current, and wherein to interpret the reconstructed eddy current to determine a measurement/object property of the metal object, said apparatus is configured to interpret the normalized and offset-removed resampled, reconstructed response.

27. A method for estimating at least one measurement/object property of a metal object, said method comprising:

generating a time-varying eddy current in a wall of the metal object utilizing a pulsed-signal transmitter;

measuring the time-varying eddy current;

fitting said time-varying measured eddy current to a parameterized polynomial;

reconstructing a smoothed version of the measured eddy current using the fitted parameters;

resampling the reconstructed eddy current using a number of sample points;

interpreting the reconstructed eddy current to determine a measurement/object property of the metal object.

28. A method in accordance with claim 27 wherein said resampling comprises logarithmic resampling.

29. A method in accordance with claim 27 wherein said resampling comprises resampling using a number of sample points approximately equal to an order of fit of the fitted parameters.

30. A method in accordance with claim 29 wherein said resampling comprises logarithmic resampling.

31. A method in accordance with claim 27 further comprising removing a DC offset from and normalizing the resampled, reconstructed response, and wherein said interpreting the reconstructed eddy current to determine a measurement/object property of the metal object comprises interpreting the normalized and offset-removed resampled, reconstructed response.

* * * * *